United States Patent [19]

Dias et al.

[11] Patent Number: 5,281,368
[45] Date of Patent: Jan. 25, 1994

[54] NORBORNENE POLYMERIZATION INITIATORS AND PROCESS FOR PREPARING SAME

[75] Inventors: Anthony J. Dias, Houston, Tex.; Sudhin Datta, Matawan; Joseph A. Olkusz, Fanwood, both of N.J.; Fred T. Morrar, Staten Island, N.Y.

[73] Assignee: Exxon Chemical Patents Inc., Linden, N.J.

[21] Appl. No.: 860,912

[22] Filed: Mar. 31, 1992

[51] Int. Cl.⁵ .............................. C07F 1/02; C08F 4/46
[52] U.S. Cl. .............................. 260/665 R; 260/350 R; 570/187; 570/215; 502/157; 502/152; 526/173
[58] Field of Search ........... 260/350 R, 665 R; 502/157, 152; 526/173, 240; 570/187, 215

[56] References Cited

U.S. PATENT DOCUMENTS

| | | | |
|---|---|---|---|
| 3,235,626 | 2/1966 | Waack | 260/881 |
| 3,390,206 | 6/1968 | Thompson | 260/875 |
| 3,478,002 | 11/1969 | Nakaguchi et al. | 260/79.5 |
| 3,506,627 | 4/1970 | Zaim | 260/80.7 |
| 3,514,500 | 5/1970 | Osmond | 260/874 |
| 3,862,077 | 1/1975 | Schulz et al. | 260/29.6 RB |
| 3,862,097 | 1/1975 | Milkovich et al. | 260/93.5 A |
| 3,862,098 | 1/1975 | Milkovich et al. | 260/93.5 A |
| 3,862,102 | 1/1975 | Milkovich et al. | 260/94.7 |
| 3,876,116 | 1/1974 | Milkovich et al. | 260/885 |
| 3,876,595 | 3/1975 | Ogura et al. | 260/80.78 |
| 3,879,494 | 1/1975 | Milkovich et al. | 360/876 R |
| 3,989,768 | 11/1976 | Milkovich et al. | 260/859 R |
| 4,039,491 | 8/1977 | Ikeda et al. | 260/4 R |
| 4,074,035 | 2/1978 | Powers et al. | 526/185 |
| 4,408,017 | 10/1983 | Martin | 525/288 |
| 4,599,384 | 7/1986 | Farona et al. | 525/245 |
| 4,890,408 | 6/1975 | Schepers et al. | 260/879 |

FOREIGN PATENT DOCUMENTS

| | | |
|---|---|---|
| 0240638 | 10/1987 | European Pat. Off. |
| 0344021 | 11/1989 | European Pat. Off. |
| 50-13483 | 2/1975 | Japan |
| 50-21513 | 7/1975 | Japan |
| 0164308 | 9/1984 | Japan ......... 526/82 |

OTHER PUBLICATIONS

Freeman et al.; J. Org. Chem., 1969, 34, 3958.
R. Waack, Polymer, vol. 2, pp. 365–366 (1961).
R. Waack, J. Org. Chem., vol. 32, pp. 3395–3399 (1967).
Huang, J. of Polym. Sci.: Part A: Polymer Chem. Ed., vol. 24, pp. 2853–2866.
Chem. Abstracts No. CA107(20)1766244.
Chem. Abstracts No. CA104(26)225321W.
Chem. Abstracts No. CA110(16)135832h.
Schutze et al.; J. Appl. Polymer Science, vol. 27, 1982, p. 4773.
Holmquist et al.; J. Appl. Polymer Science, vol. 15, 1971, pp. 2103–2114.
Norton et al.; Marcomolecules, 1989, vol. 22, pp. 1022–1025.
Hill et al.; J. Org. Chem. 1989, vol. 54, pp. 5286–5292.
Marco Molecules, an Introduction to Polymer Science, Ed Bovey et al.; Academic Press, New York, 1979, pp. 92–95.
Kirkothmer Encyclopedia of Polymer Tech., vol. 21, John Wiley & Sons, 1983, p. 820.

Primary Examiner—Fred Teskin
Attorney, Agent, or Firm—Catherine L. Bell; Myron B. Kurtzman

[57] ABSTRACT

The present invention relates to a novel compound, its use as an initiator in anionic polymerizations yielding norbornene-terminated homopolymers of block copolymers, and the further use of said norbornene-terminated polymers as macromonomers in the preparation of graft copolymers.

12 Claims, No Drawings

NORBORNENE POLYMERIZATION INITIATORS AND PROCESS FOR PREPARING SAME

BACKGROUND OF THE INVENTION

1. Field of the Invention

The present invention relates to a novel compound, its use as an initiator in anionic polymerizations yielding norbornene-terminated homopolymers of block copolymers, and the further use of said norbornene-terminated polymers as macromonomers in the preparation of graft copolymers.

2. Description of Related Art

Anionic polymerization proceeds by attack on a vinyl monomer of a basic (nucleophilic) species resulting in the heterolytic splitting of the double bond to produce a carbon anion followed by propagation of this ion. The most common initiators used in such polymerization reactions are the alkyl and aryl derivatives of alkali metals, particularly lithium alkyls. Organolithium initiators are particularly preferred since they are readily prepared by reaction of the lithium metal with alkyl or aryl halides and are soluble in the hydrocarbon solvents used in their preparation as well as solvents used in solution polymerization reactions. N-butyl lithium and sec-butyl lithium are generally preferred initiators used for the anionic polymerization of vinyl and diolefin monomers including vinyl aromatic monomers, acrylic and methacrylic monomers and diolefin monomers such as butadiene or isoprene. A representative detail of organo-lithium initiators and their method of preparation appears in U.S. Pat. No. 3,890,408.

In a further development of this chemistry, organolithium initiators containing vinyl unsaturation have been used to initiate polymerization of anionically polymerizable monomers to produce vinyl terminated macromolecules which may be then used as a macromeric component in the preparation of copolymers by ionic or free radical polymerization techniques to produce graft copolymers containing the vinyl macromonomer which provides the pendant graft chains. For example, U.S. Pat. No. 3,235,626 to Waack, assigned to Dow Chemical Company, describes a method for preparing graft copolymers of controlled branch configuration. It is described that the graft copolymers are prepared by first preparing a prepolymer by reacting a vinyl metal compound with an olefinic monomer to obtain a vinyl terminated prepolymer. After protonation and catalyst removal, the prepolymer is dissolved in an inert solvent with a polymerization catalyst and is thereafter reacted with either a different polymer having a reactive vinyl group or a different vinyl monomer under free-radical conditions.

This art suffers from two major limitations: 1) Though the use of vinyl lithium guarantees that each polymer chain has one vinyl end group, it is recognized and documented in the literature, such as R. Waack et al., Polymer, Vol. 2, pp. 365-366 (1961) and R. Waack et al. J. Org. Chem., Vol. 32, pp. 3395-3399 (1967), that vinyl lithium is one of the slowest anionic polymerization initiators. This slow initiation rate when used to polymerize styrene produces a polymer having a broad molecular weight distribution (Mw/Mn greater than 2), as a consequence of the ratio of the overall rate of propagation of the styryl anion to that of the vinyl lithium initiation. As a result, graft copolymers prepared from these macromonomers cannot have a uniform side chain molecular weight. 2) It is well known in the art that substituted vinyl compounds do not generally polymerize to high conversions. Conversion tends to decrease as the length of the side chain increases. Conversions of 50%, high for most substituted vinyls, will mean that the resulting graft copolymers will contain 50% of unreacted macromonomer. For most applications this level of ungrafted polymer is unacceptable.

A different approach towards the preparation of macromonomers containing terminal unsaturated functional groups is also disclosed in the art.

Sumitomo Chemical's Japanese Kokai 50013483-A discloses olefin copolymers prepared by the Ziegler-catalyzed reaction of ethylene and/or propylene and polystyrene end-capped with norbornene. The preparation of a styrene-ethylene graft copolymer is described in an example, wherein the polystyrene macromonomer is formed by reacting living n-BuLi capped polystyrene with 5-bromomethyl-2-norbornene.

In addition, polystyrene macromonomers capped with a norbornene group have been prepared by coupling a polystyrene anion with 5-bromomethyl norbornene in a mixed solvent (Chemical Abstracts No. CA104 (26) 225321 w, 1986) and these functional polystyrenes have been further disclosed used as a comonomer in the Ziegler-Natta polymerization of graft copolymers comprising a polyethylene backbone containing grafted polystyrene side chains (Chemical Abstracts No. CA107(20) 176624y, 1987).

Functionalized macromolecules are also disclosed by R. Milkovich et al. in U.S. Pat. No. 3,989,768 as well as in R. Milkovich et al. J. Appl. Polym. Sci., Vol. 27, 1982, pg. 4773. This work describes anionic polymerization of a number of monomers with active initiators, thereby forming monodisperse living polymer chains. These living chains are then reacted with a wide-range of termination agents to introduce substantially end-functionalized macromonomers. This route clearly improves the resulting macromer polydispersity and allows for a broader range of end functionality, but it introduces an uncertainty into the "purity" of the end-functional groups. One can no longer be assured that each and every chain has one functional group. For example, the synthesis of norbornenylpolystyrene in accordance with the Milkovich journal article involves as step 1, the anionic polymerization of styrene in benzene using secondary-butyl lithium as initiator. This step, if done correctly, can be substantially free of termination. However in practice it is usually about 95% free of termination. Step 2 involves introducing ethylene oxide into the polymerization vessel to give the alkoxide. Once again this is about 95% efficient. Step 3 involves the reaction of 5-norbornene-2-carbonyl chloride with the polystyrene alkoxide. This step is perhaps at best 95% efficient. Though each step results by any standards in excellent yields together they represent a polymer that is 0.95×0.95×0.95=86% end functional. Analytical techniques still have not reached the level of precision necessary to characterize this level of end-functionality of high molecular weight macromers. The most informative characterization comes from analysis of the graft copolymers produced using these macromers.

Synthesis of the graft copolymers using these macromers was presented in Milkovich U.S. Pat. No. 3,989,768 with very limited graft copolymer characterization information. A recent paper, B. Huang et al., J. of Polymer Science: Part A: Polymer Chemistry Edition, Vol. 24, 1986, pgs. 2853-2866 utilized the vinyl terminated macromer as described in U.S. Pat. No. 3,989,768 to prepare graft copolymers of ethylene and propylene. This work highlights two important points: First that double bond titrations can only give an approximation for end-group functionality and the best accuracy one can hope for is 20%. Second that the best conversions for vinyl terminated polystyrene macromonomers with a moderate molecular weight and useful feed compositions (10 to 30% on EP) is 40%.

In light of the above work, it is clearly highly desirable to devise a means for preparing macromonomers wherein the guaranteed functionality introduced in the initiation step is combined with a more active polymerization group. Also, in view of the utility of graft polymers of anionically polymerized macromonomers with alpha-olefin base polymers and particularly in view of the limitations and uncertainties in the prior art methods of preparing them, there exists an ongoing need for new and efficient means of preparation of graft polymers having essentially uniform molecular weight side chains. It is thus an object of this invention to provide novel compounds, novel macromolecules, and novel graft copolymers as well as novel means of preparation that allow for both rapid initiation of the anionically polymerized macromonomers and maximization of their functionalization for subsequent graft copolymerization.

SUMMARY OF THE INVENTION

The present invention relates to the synthesis and use of alkali-metallated alkyl substituted norbornenes as ionic initiators in the polymerization of anionically polymerizable monomers of monomer mixtures such as vinyl or vinylidene monomers. The polymers produced may be characterized as macromonomers containing a single norbornene group at the head of the polymer chain. This initiator provides for rapid initiation as compared with propagation and results in high monomer conversion and provides macromonomers having a very narrow molecular weight distribution (Mw/Mn = 1.25 or less) having 100% terminal norbornene functionality.

The present invention also relates to random graft copolymers prepared by copolymerizing the macromonomer described above with one or more monomers normally copolymerizable with norbornene monomeric material using free radical, anionic or cationic polymerization techniques.

DETAILED DESCRIPTION OF THE INVENTION

The broad category of compounds provided in accordance with this invention are alkyl-substituted norbornenes represented the general formula I:

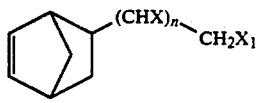

wherein n is o or an integer ranging from 1-17, X and $X_1$ are independently selected from the group consisting of H, Li, K and Na, provided that where $X_1$ is Li, K or Na, then X is H, further provided that where $X_1$ is H, then n is an integer ranging from 1-17, (n-1) of the X substituents are also H, and X is Li, K or Na and further provided that where n is o, then $X_1$ is Li, K or Na.

These compounds may be generally prepared by contacting dicyclopentadiene with a mono-halogen containing olefinically unsaturated alkyl compound containing from 3 to 20 carbon atoms under Diels-Alder reaction conditions to form the addition product which is an alkyl norbornene containing a halogen substituent group on the alkyl chain. This reaction product may then be reacted under specified conditions with an alkali metal such a lithium, sodium or potassium such that the halogen atom is displaced to form the alkali-metallated, alkyl substituted norbornene compound of this invention.

Suitable halogen-substituted olefins which may be employed to form the Diels-Alder adduct include allyl bromide, 3-chloro-1-butene, 3-bromo-1-pentene, 1-chloro-2-butene, 5-chloro-1-pentene, 3-chloro-1-propene, 4-bromo-1-butene and 2-chloro-1-butene.

The preferred compounds for the purposes of this invention are those set forth in formula I above wherein n is o and $X_1$ is Li, K or Na. These are preferred because they are readily synthesized using a relatively inexpensive and available reactant (allyl bromide) and the resulting intermediate alkyl norbornene halide is recovered in relatively high yields because of a minimization of side reactions including decomposition and unwanted cyclization reactions. Accordingly while the invention will be further described with a focus on preferred compounds and their method of preparation, it should be understood that such description is equally applicable to the preparation of other compounds within the scope of formula I above.

The preferred anionic compounds, useful as initiators, provided in accordance with this invention may be generally described as corresponding to the formula II.

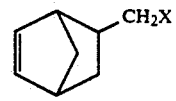

wherein X is an alkali metal selected from the group consisting of lithium, potassium and sodium. The preferred metal is lithium since the lithium containing compound can be more readily prepared by simple lithiation of the corresponding 2-halomethyl-5-norbornene compound and is quite soluble in solvents used for anionic polymerization reactions.

The compounds may be typically prepared by a two stage process. In the first stage an allyl halide, preferably allyl bromide, may be reacted with cyclopentadiene to give the bicycloheptenyl-2 methyl halide derivative, i.e., 2-halomethyl-5-norbornene. The reaction may be carried out using cyclopentadiene as a solvent and at a temperature of from about 20° to 100° C. A second alternative first stage process involves refluxing the allyl halide with dicyclopentadiene whereby at high reflux temperatures (170°-190° C.) dicyclopentadiene dissociates to form cyclopentadiene, which then adds to the allyl halide. Reaction times under either process may vary between 2 and 8 hours. Although stoichiometric quantities or an excess of either reactant may be employed, it is preferred to use a slight excess of the allyl halide reactant.

The crude product of the first stage reaction is then purified using conventional distillation techniques to further separate the 2-halomethyl-5-norbornene from unreacted reactant and isomers thereof.

The second stage of the preparation of the compound involves the reaction of lithium, sodium or potassium metal with the 2-halomethyl-5-norbornene to form the 2-metalomethyl-5-norbornene having the structure of formula I above. This reaction is conducted in a solvent which is inert under reacting conditions and which is free of materials which are detrimental to the reaction such as water, oxygen, carbon dioxide and/or alcohols. Suitable solvents which may be used are aromatic hydrocarbons such as benzene, toluene, xylene, ethyl benzene, t-butyl benzene and the like; saturated aliphatic and cycloaliphatic hydrocarbons such as n-hexane, n-heptane, n-octane, cyclohexane and the like; aliphatic and cyclic ethers such as dimethyl ether, diethyl ether, dibutyl ether, tetrahydrofuran, dioxane, anisole, tetrahydropyran, diglyme and the like. Organic ethers are preferred solvents due to higher rates of reaction in ether medium. The reaction is best conducted by gradual drop-wise addition of the norbornene compound to a finely divided suspension of the metal present in excess and in solvent. The reaction is preferably conducted at temperatures below 0° C., preferably below −30° C., and reaction times may vary between about 3 to 8 hours. These reaction conditions are especially important to avoid thermally induced ring cleavage reactions and unwanted addition reactions which can lead to a low yield of the desired product as well as the formation of isomers which are difficult to separate. Under these preferred conditions, essentially all of the bromomethyl norbornene is reacted to give a mixture which is substantially the lithiomethyl norbornene containing less than 5% by weight of unidentified oligomeric products. The reaction product may then be covered by filtering out residual metal particles and removal of the solvent by evaporation. The following examples illustrate the preparation and purification of 2-bromomethyl-5-norbornene, and the lithiation thereof to produce 2-lithiomethyl-5-norbornene.

EXAMPLES

Example 1

Synthesis of 2-bromomethyl-5-norbornene

A 1 liter steel reaction vessel, fitted with a 2000 kpa pressure release safety and a steel plug was used for the Diels-Alder reaction. 264.4 g (4 moles) Dicyclopentadiene (Aldrich), 532.4 g (4.4 moles) allyl bromide (Aldrich Gold Label which was purified by passing it through a column containing sodium bicarbonate then magnesium sulfate), 3.9 g hexadecane (GC internal standard) and 0.5 g butylated hydroxytoluene (antioxidant) were placed into the reactor and reacted 6 hours at 180° C. The resulting crude mixture contained 75% 2-bromomethyl-5-norbornene, 9% dicyclopentadiene, 3% allylbromide and unidentified isomers of each.

Example 2

Synthesis of 2-Bromomethyl-5-norbornene

A 1 liter steel reaction vessel, fitted with a 2000 kpa pressure release safety and a steel plug was used for the Diels-Alder reaction. 264.4 g (4 moles) Dicyclopentadiene (Aldrich), 580.8 g (4.8 moles) allyl bromide (Aldrich Gold Label which was purified by passing it through a column containing sodium bicarbonate then magnesium sulfate), 3.9 g hexadecane (GC internal standard) and 0.5 g BHT were placed into the reactor and reacted 6 hours at 180° C. The resulting crude mixture contained 78% 2-bromomethyl-5-norbornene, 2% dicyclopentadiene, 7% allylbromide and unidentified isomers of each.

Example 3

Purification of 2-Bromomethyl-5-norbornene

The crude reaction mixture from Examples 1 and 2 were combined and purified by two distillation steps. The first distillation was conducted in a 3 liter 3 neck flask fitted with a nitrogen sweep, a thermocouple, and an efficient column. The system pressure was kept at 700 mm Hg pressure and the pot temperature was slowly raised to 175° C. Under these conditions the dicyclopentadiene cracked and cyclopentadiene codistilled with the allyl bromide. When it appeared that no more volatile products were distilling the pressure was dropped and the contents of the flask were flashed into a receiver. This distillate contained 2% dicyclopentadiene, 95% 2-bromomethyl-5-norbornene and higher boiling unidentified isomers. This receiver was then fractionally distilled at 13 mm. Several fractions were obtained ranging from 99.8 to 96% 2-bromomethyl-5-norbornene (by GLC) giving an overall purified yield of 60%.

Example 4

Lithiation of 2-bromomethyl-5-norbornene

A 2 liter 2 neck flask, fitted with a stirrer and a septum inlet was assembled in a dry box. 700 ml of diethyl ether (distilled from dibutylmagnesium) was placed in the flask along with 4 g lithium (Lithco, 0.8% sodium, slivered from rod). The flask was stoppered and 5% of a solution of 38 g 2-bromomethyl-5-norbornene was added. As soon as the reaction began the flask was cooled to −50° C. or below. The addition was continued dropwise at −50° over 6 hour period. An aliquot was removed and analyzed by GLC; the bromide was quantitatively converted to 2-lithiomethyl-5-norbornene (90%) 2-methyl-5-norbornene was found after reaction with methanol). The excess lithium was removed by passing the mixture through a frit and the ether was removed under vacuum via rotary evaporation at −50° C. The 2-lithiomethyl-5-norbornene (LMNB) was redissolved in cyclohexane to give a solution that was approximately 1 molar in organolithium.

Living polymers are conveniently prepared by contacting an anionically polymerizable monomer or mixture of monomers with the lithiomethyl norbornene compound prepared as above in the presence of an organic solvent which does not participate in or interface with the polymerization reaction. The living polymers prepared in accordance with this invention using LMNB as an initiator may be generally characterized by the structure III:

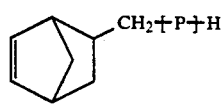   III wherein P represents a linear polymeric chain which may be a homopolymer, random copolymer or block copolymer derived from anionically polymerizable monomeric material. This structure is in contrast to prior polymers prepared by coupling a living polymer prepared using a butyl lithium initiator capped by a termination reaction with a norbornene alkyl halide such as disclosed in U.S. Pat. No. 3,862,077 and the Chemical Abstract publications cited above and represented by the structure:

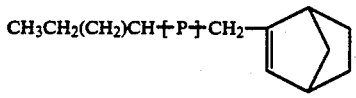

Those monomers susceptible to anionic polymerization are well-known and the present invention contemplates the use of all anionically polymerizable monomers. Non-limiting illustrative species include vinyl aromatic compounds, such as styrene, alpha-methylstyrene, vinyl toluene and its isomers; vinyl unsaturated amides such as acrylamide, methacrylamide, N,N-dialkyl acrylamides, e.g., N,N-dimethylacrylamide; acenaphthalene; 9-acrylcarbazole; acrylonitrile and methacrylonitrile, organic diioscyanates including lower alkylene, phenylene and toluene diisocyanates; lower alkyl and allyl acrylates and methacrylates, including methyl, t-butyl acrylates and methacrylates; lower olefins, such as ethylene propylene, butylene, isobutylene, pentene, hexane, etc; vinyl esters of aliphatic carboxylic acids such as vinyl acetate, vinyl propionate, vinyl octoate, vinyl stearate, vinyl benzoate; vinyl lower alkyl ethers; vinyl pyridines, vinyl pyrrolidones; and dienes including isoprene and butadiene. The term "lower" is used above to denote organic groups containing 8 or fewer carbon atoms. The preferred olefinic containing monomers are conjugated dienes containing 4 to 12 carbon atoms per molecule and the vinyl-substituted aromatic hydrocarbons containing up to about 12 carbon atoms.

Many other monomers suitable for the preparation of the side chains by anionic polymerization are those disclosed in macromolecular Reviews: Volume 2, pages 74–83, Interscience Publishers, Inc. (1967), entitled "Monomers Polymerized by Anionic Initiators," the disclosure of which is incorporated herein by reference.

The first step of this process is carried out by reacting a mono-functional lithium metal compound system with the respective monomer or monomers to form the living polymer chain P-Li. This polymerization step can be carried out in one step or in a sequence of steps. In the case where the polymer chain P is a homopolymer or a random or tapered copolymer of two or more monomers, the monomers are simultaneously polymerized with the lithium metal initiator. In the case where the polymer chain P is a block copolymer comprising two or more homo- or copolymers blocks, these individual blocks can be generated by incremental or sequential monomer addition.

An inert solvent generally is used to facilitate heat transfer and adequate mixing of initiator and monomer Hydrocarbons and ethers are the preferred solvents. Solvents useful in the anionic polymerization process include the aromatic hydrocarbons such as benzene, toluene, xylene, ethylbenzene, t-butylbenzene, etc.

Also suitable are the saturated aliphatic and cycloaliphatic hydrocarbons such as n-hexane, n-heptane, n-octane, cyclohexane and the like. In addition, aliphatic and cyclic ether solvents can be used, for example, dimethyl ether, diethyl ether, dibutyl ether, tetrahydrofuran, dioxane, anisole, tetrahydropyran, diglyme, glyme, etc. The rates of polymerization are faster in the ether solvents than in the hydrocarbon solvents.

The amount of initiator is an important factor in anionic polymerization because it determines the molecular weight of the living polymer. If a small proportion of initiator is used, with respect to the amount of monomer, the molecular weight of the living polymer will be larger than if a large proportion of initiator is used. Generally, it is advisable to add initiator dropwise to the monomer (when that is the selected order of addition) until the persistence of the characteristic color of the organic anion, then add the calculated amount of initiator for the molecular weight desired. The preliminary dropwise addition serves to destroy contaminants and thus permits better control of the polymerization.

To prepare a polymer of narrow molecular weight distribution, it is generally preferred to introduce all of the reactive species into the system at the same time. By this technique, polymer growth by consecutive addition of monomer takes place at the same rate to an active terminal group, without chain transfer or termination reaction. When this is accomplished, the molecular weight of the polymer is controlled by the ratio of monomer to initiator, as described in the formula: Molecular weight of living polymer=(Moles of Monomer/Moles of Initiator)×Molecular weight of Monomer.

As it can be seen from the above formula, high concentrations of initiator leads to the formation of low molecular weight polymers, whereas, low concentrations of initiator leads to the production of high molecular weight polymers.

The concentration of the monomer charged to the reaction vessel can vary widely, and is limited by the ability of the reaction equipment to dissipate the heat of polymerization and to properly mix the resulting viscous solutions of the living polymer. Concentrations of monomer as high as 50 percent by weight or higher based on the weight of the reaction mixture can be used. However, the preferred monomer concentration is from about 5 to about 25 percent in order to achieve adequate mixing.

As can be seen from the formula above and the foregoing discussion on the concentration of the monomer, the initiator concentration is critical, but may be varied according to the desired molecular weight of the living polymer and the relative concentration of the monomer. Generally, the initiator concentration can range from about 0.0001 to about 0.1 mole of active alkali metal per mole of monomer, or higher. Preferably, the concentration of the initiator will be from about 0.01 to about 0.004 mole of active alkali metal per mole of monomer.

The temperature of the polymerization will depend on the monomer. Generally, the reaction can be carried out at temperatures ranging from about −100° C. When using aliphatic and hydrocarbon solvents, the preferred temperature range is from about −10° C. to about 100° C. With ethers as the solvent, the preferred temperature range is from about −100° C. to about 100° C. The polymerization of styrene monomer, for example is generally carried out at slightly above room temperature,; the polymerization of alpha-methylstyrene monomer preferably is carried out at lower temperatures, e.g., −80° C.

The preparation of the living polymer can be carried out by adding a solution of the alkali metal hydrocarbon initiator in an inert organic solvent to a mixture of monomer and diluent at the desired polymerization temperature and allowing the mixture to stand with or without agitation until the polymerization is completed. An alternative procedure is to add monomer to a solution of the catalyst in the diluent at the desired polymerization temperature at the same rate that it is being polymerized. By either method the monomer is converted quantitatively to a living polymer as long as the system remains free of impurities which inactivate the anionic species. As pointed out above, however, it is preferred to add all of the reactive ingredients together rapidly to insure the formation of a uniform molecular weight distribution of the polymer.

The anionic polymerization must be carried out under carefully controlled conditions so as to exclude substances which destroy the catalytic effect of the catalyst or initiator. For example, such impurities as water, oxygen, carbon monoxide, carbon dioxide, and the like should be excluded from the system. Thus, the polymerizations are generally carried out in dry equipment, using anhydrous reactants, and under an inert gas atmosphere, such as nitrogen, helium, argon, methane, and the like.

The above-described living polymers are susceptible to further reactions including further polymerization. Thus, if additional monomer, such as styrene, is added to the living styryl polymer, the polymerization is renewed and the chain grows until no more monomeric styrene remains. Alternatively, if another different anionically polymerizable monomer is added, such as butadiene or ethylene oxide, the above-described living polymer initiates the polymerization of the butadiene or ethylene oxide and the ultimate living polymer which results consists of a polystyrene segment and a polybutadiene or polyoxyethylene segment.

A poly(styrene-ethylene) block copolymer can be prepared by contacting living polystyrene with ethylene in the presence of a compound of a transition metal of Group V-VIII in the periodic table, e.g., titanium tetrachloride. This technique is also applicable to other alpha-olefins such as propylene, butene, etc. The resulting copolymer is still a living polymer and can be terminated by the methods in accordance to the practice of the present invention.

As noted above, the living polymers employed in the present invention are characterized by relatively uniform molecular weight, i.e., the distribution of molecular weights of the mixture of living polymers produced is quite narrow. This is in marked contrast to the typical polymer, where the molecular weight distribution is quite broad. The difference in molecular weight distribution is particularly evident from an analysis of the gel permeation chromatogram of commercial polystyrene (Dow '666) prepared by free-radical polymerization and polystyrene produced by the anionic polymerization process utilized in accordance with the practice of the present invention.

After the desired degree of polymerization is reached, the polymerization is terminated by contact of the ionic polymer with agents containing active hydrogen (proton donors) such as water, alcohols, aqueous acid solutions or mixtures thereof. An antioxidant such as butylated hydroxytoluene (BHT) may also be added to the reaction mixture before isolation of the final polymer.

The molecular weight (Mw) of the living polymers produced in accordance with this invention may generally range from about 1,000 up to about 2,000,000 preferably from about 5,000 up to about 500,000 and most preferably from about 10,000 up to about 150,000. As stated above, 2-lithiomethyl-5-norbornene provides for rapid initiation of the anionic reaction mechanism thereby leading to polymers having a very narrow molecular weight distribution (Mw/Mn) of less than 1.25, generally in the order of 1.1 or less. As such, the polymers have enhanced mechanical and processing properties.

The following examples illustrates the preparation of a 2-polystyryl-5-norbornene polymer having the structure of formula IV:

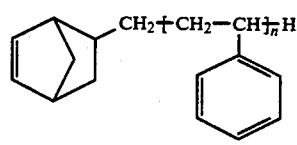

wherein n is an integer sufficient to provide a polymer molecular weight of about 5,000 to about 75,000; generally in the range of from about $n=50$ to $n=600$.

All reactions and reagents were handled under an inert atmosphere of nitrogen with careful exclusion of both oxygen and water. The monomers were purified by distillation within a day of polymerization from dibutylmagnesium. The solvent (heptane, cyclohexane, ether or tetrahydrofuran) was purified the day of the polymerization by distillation under nitrogen of 25% of the total volume or alternatively by vacuum distillation from butyl lithium. The monomer was added to the solvent just prior to use. All glassware, syringes and needles were oven dried at 150° C. for 3 hours. The hot glassware, syringes and needles were oven dried at 150° C. for 3 hours. The hot glassware was cooled and assembled under inert atmosphere usually in a dry box.

Example 5

Preparation of 2-(Polystyryl)-5-norbornene

A 3 liter flask was fitted with a magnetic stirring bar and filled with 2800 ml cyclohexane. The flask was heated and 600 ml cyclohexane was distilled and the flask was cooled. 250 g freshly distilled styrene (from dibutylmagnesium) was added along with 80 ml of the 2-lithiomethyl-5-norbornene solution from Example 4. The polymerization began instantaneously and the flask temperature rose from 35° C. to 55° C. at which temperature it was maintained for 3 hours. The polymerization was terminated with methanol vapor and 0.1 g BHT was added before the polymer was isolated by precipitation in isopropanol. The resulting norbornene terminated polystyrene (240 g) had a $Mw=6600$, $Mn=5700$ and $Mw/Mn=1.1$.

Example 6

Preparation of 2-(Polystyryl)-5-norbornene

The experiment was repeated as in Example 5. This time 90 g of styrene was reacted with 3 ml 2-lithiomethyl-5-norbornene. The resulting polymer (85 g) has a Mw of 73,000, and Mn of 69,00 and a Mw/Mn of 1.06.

Norbornene is a very reactive monomer, in many cases as reactive as ethylene, and may therefore be readily copolymerized with other monomers in free radical, anionic and cationic polymerization systems, as well as in extruder graft reactions. This characteristic allows the utilization of the norbornene-capped macromonomers of this invention in similar copolymerization reactions for the preparation of random graft copolymers containing the norbornene head monomer as part of the copolymeric backbone chain and the polymer associated therewith present as graft polymer segments of essentially uniform molecular weight pendant from the backbone chain, such as recurring polymer units represented by the structure V:

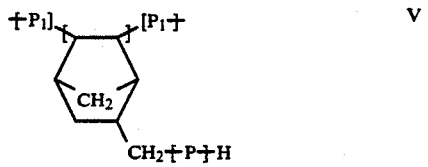

wherein $P_1$ represents a polymer or copolymer segment derived from a monomer or mixtures of monomers copolymerizable with norbornene-type monomers and P is as described above.

The preparation of such graft copolymers provides thermoplastic polymer compositions having balanced beneficial properties of both the P and $P_1$ polymer components alone and provides a technique for chemically linking these polymers with might otherwise be mutually incompatible when physically mixed or grafted by other techniques. The present graft copolymers differ structurally from conventional graft copolymers since the macromolecular monomer is interposed between polymeric segments of the backbone polymer rather than being arbitrarily attached to the backbone in a random manner. These characteristics contribute materially to the advantageous properties which inure in these novel graft copolymers.

The backbone component of the graft copolymers of the present invention may be derived from any ethylenically unsaturated monomer which is copolymerizable with norbornene-type monomer materials. These include alpha-olefin monomers containing from 2 to about 8 carbon atoms such as ethylene, propylene, 1-butene, isobutene, 1-pentene, 1-hexane, and the like as well as mixtures of ethylene and one or more of said olefins. Also include are diolefin monomers such as butadiene, isoprene, piperylene and other conjugated dienes as well as mixtures of olefin and diolefin monomers such as isobutylene and isoprene which can be used to make so called butyl rubber; mixtures of butadiene or isoprene an vinyl aromatic monomers such as styrene or other vinyl monomers such as acrylonitrile or lower alkyl (meth) acrylates.

Other monomers which may be employed in preparing the backbone polymer include the acrylic acids, their esters, amides and nitriles including acrylic acid, methacrylic acid, the alkyl esters of acrylic and methacrylic acid, acrylonitrile, methacrylonitrile, acrylamide, methacrylamide, N,N-dimethacrylamide; the vinyl halides such as vinyl chloride, and vinylidene chloride; the vinyl cyanides such as vinylidene cyanide; vinyl esters such as vinyl acetate, vinyl propionate and vinyl chloroacetate, etc, and the vinylidene containing dicarboxylic anhydrides, acids an esters, fumaric acid and esters, maleic anhydrides, acids and esters thereof.

Particularly preferred backbone monomer material includes ethylene, propylene, isobutene, mixtures of ethylene and alpha-olefins including propylene, butene, pentene, hexane, heptene, octene, alkyl acrylates or methacrylates wherein the alkyl group contains 1 or 2 carbon atoms and conjugated diolefins such as butadiene or isoprene, alone or mixed with a vinyl monomer such as styrene, acrylonitrile or a lower alkyl acrylate or methacrylate. Especially preferred backbone monomer is a mixture of ethylene and propylene present at a level such that the copolymer backbone contains from about 15 to about 80 mole percent polymerized ethylene, the balance being propylene and the interpolymerized norbornene head monomer of the macromonomer.

The weight average molecular weight of the graft copolymers prepared in accordance with this invention may generally range from about 10,000 up to about 3,000,000, more preferably in the range of from about 10,000 up to about 250,000.

The copolymerization of the polymerizable macromolecular monomers with the comonomers may be conducted in a wide range of proportions. Generally speaking, a sufficient amount of the macromolecular monomer should be present to provide the chemical joining of at least one of the uniform molecular weight side chain polymers to each backbone polymer, so that a noticeable effect on the properties of the graft copolymeric properties can be obtained. Since the molecular weight of the polymerizable macromolecular monomer generally exceeds that of the polymerizable comonomers, a relatively small amount of the polymerizable macromolecular monomer can be employed. However, chemically joined, phase separated thermoplastic graft copolymers may be prepared by copolymerizing a mixture containing up to about 95 percent by weight, or more, of the polymerizable macromolecular monomers of this invention, although mixtures containing up to about 60 percent by weight of the polymerizable macromolecular monomer are preferred. Stated, otherwise, the resinous thermoplastic chemically joined, phase separated graft copolymer of the invention is comprised of (1) from 1 to about 95 percent by weight of the polymerizable macromolecular monomer having a narrow molecular weight distribution (i.e., a Mw/Mn of less than 1.1); and (2) and from 99 to about 5 percent by weight of a copolymerizable comonomer or mixture of comonomers define herein above.

The polymerizable macromolecular monomers copolymerize with the herein above referred to comonomers in bulk, in solution, in aqueous suspension and in aqueous emulsion systems suitable for the particular polymerizable macromolecular monomer, its end group and the copolymer employed. If a catalyst is employed, the polymerization environment suitable for the catalyst should be employed. For example, oil-or solvent-soluble peroxides such as benzoyl peroxide are generally effective when the polymerizable macromolecular monomer is copolymerized with a ethylenically unsaturated comonomer in bulk, in solution in an organic solvent benzene, cyclohexane, hexane, toluene and the like, or in aqueous suspension, water soluble peroxides such as such as sodium, potassium, lithium and ammonium persulfates are useful in aqueous suspension and emulsion systems. In the copolymerization of polymerizable macromolecular monomers and a polystyrene, polyisoprene or polybutadiene repeating unit, an emulsifier or dispersing agent may be employed in aqueous suspensions systems. In these systems, particular advantage can be achieved by dissolving the water-insoluble polymerizable macromolecular monomer in a small amount of suitable solvent such as a hydrocarbon. By this technique, the comonomer copolymerizes with the macromolecular monomer in the solvent, in an aqueous system surrounding the solvent-polymer system. Of course, the polymerization catalyst is chosen such that it will be soluble in the organic phase of the polymerization system.

As previously stated, various different catalyst systems can be employed in the present invention for the copolymerization process. For example, ethylene polymerizes under free-radical, cationic and coordination polymerization conditions; propylene and higher alpha-olefins only polymerize under coordination polymerization conditions; isobutylene only polymerizes under cationic polymerization conditions; the dienes polymerize by free-radical anionic and coordination polymerization conditions; styrene polymerizes under free-radical, cationic, anionic and coordination conditions; vinyl chloride polymerizes under free-radical and coordination polymerization conditions; vinylidene chloride polymerizes under free-radical polymerization conditions; vinyl fluoride polymerizes under free-radical conditions; tetrafluoroethylene polymerizes under free-radical and coordination polymerization conditions; vinyl ethers polymerize under cationic and coordination polymerization conditions; vinyl esters polymerize under free radical polymerization conditions; acrylic and metacrylic esters polymerize under free-radical, anionic and coordination polymerization conditions; and acrylonitrile polymerizes under free-radical, anionic and coordination polymerization conditions.

It will be understood by those skilled in the art that the solvent, reaction conditions and feed rate will be partially dependent upon the type of catalyst system utilized in the copolymerization process. One of the considerations is that the macromolecular monomer be dissolved in the solvent system utilized.

It is not necessary, however, for the monomer feed to be soluble in the solvent system. Generally, under these conditions during the formation of the copolymer, the graft copolymer will precipitate out of the solvent wherein it can be recovered by techniques known in the polymer art.

The temperature and pressure conditions during the copolymerization process will vary according to the type of catalyst system utilized. Thus, in the production of low density polyolefin backbones under free-radical conditions, extremely high pressures will be employed. On the other hand, the high density substantially linear polyolefin backbone polymers produced by the coordination type catalyst generally will be prepared under moderately low pressures.

When preparing graft copolymers having a polyolefin backbone of ethylene or propylene together with a macromolecular monomer, it is preferred to employ a coordination catalyst known in the art as the Ziegler catalyst and Natta catalysts, the latter being commonly used for polypropylene. Some of these catalysts are disclosed in Belgian Pat. No. 533,362, issued May 16, 1955, and U.S. Pat. Nos. 3,113,115 and 3,257,332 to Ziegler et al. These catalysts are prepared by the interaction of a compound of transition metals of group IV-VII in the period table, the catalyst and an organometallic compound derived from group I-III metals, as co-catalyst. The latter are compounds such as metal hydrides and alkyls capable of giving rise to hydride ions or carbanions, such as trialkyl aluminum. Compounds of the transition elements have a structure with incomplete d-shells and in the lower valence states, can associate with the metal alkyls to form complexes with highly polarized bonds. Those elements are preferably titanium, chromium, vanadium, and zirconium. They yield the best Ziegler catalysts by reaction of their compounds with metal alkyls.

As previously stated, the solvent system utilized will most conveniently be the solvent employed in the preparation of the macromolecular monomer. Solvents useful for the polystyrene macromolecular monomers are those which dissolve polystyrene. Typical solvents for polystyrene include cyclohexane, benzene, toluene, xylene, decalin, tetralin and the like.

The polymerization reaction may be conducted at any suitable temperature, depending on the particular catalyst, macromolecular monomer feed, resulting graft copolymer and solvent used. Generally, the graft copolymerization will be conducted at a temperature of from about 10° C. to about 500° C., preferably from about 20° C. to about 100° C.

The graft copolymerization reaction is preferably conducted by placing a predetermined amount of the macromolecular monomer dissolved in the appropriate solvent in the reactor. The polymerization catalyst and monomer are thereafter fed into the solvent system to produce the graft copolymer.

It is generally desirable to provide a graft copolymer having at least about 2 percent macromolecular monomer incorporated in the backbone polymeric material. However, satisfactory results can be obtained with up to about 40 percent by weight macromolecular monomer incorporation.

The means for providing the proper amount of incorporation of the macromolecular monomer can be determined simply by adding the appropriate weighed macromolecular monomer used in the copolymerization process. For example, if a graft copolymer having 10 percent by weight incorporation of the macromolecular monomer into the backbone polymer is desired, one simply employs 10 parts by weight of the macromolecular monomer for each 90 parts by weight of the monomer feed.

Following the procedures outlined above, graft copolymers having unique combinations of properties are produced. These unique combinations of properties are made possible by the novel process herein which provides for compatibility of otherwise incompatible polymeric segments. These incompatible segments segregate into phases of their own kind.

The chemically joined, phases separated graft copolymers of the invention microscopically possess a controlled dispersion of the macromolecular side chain in one phase (domain) within the backbone polymer phase (matrix). Because all of the macromolecular monomer side chain domains are an integral part or interposed between large segments of the backbone polymer, the resulting graft copolymer will have the properties of a cross-linked polymer, if there is a large difference in the Tg or Tm of the backbone and side chain segments. This is true only up to the temperature required to break the thermodynamic cross-link of the dispersed phase. In essence, a physically cross-linked (as opposed to chemical cross-linked) type polymer can be made that is reprocessable and whose properties are established by simple cooking, rather than vulcanization or chemical cross-linking.

Although, as indicated, the graft copolymers herein are characterized by a wide variety of physical properties, depending on the particular monomers used in their preparation, and also on the molecular weights of the various polymer segments within a particular graft copolymer, all of these graft copolymers are useful, as tough, flexible, self-supporting films. These films may be used as food-wrapping material, protective wrapping for merchandise displayed for sale, molded articles having improved impact strength and like applications.

Graft copolymers of the macromolecular monomer, polystyrene, with ethylene-propylene, isobutylene, or propylene oxide monomers have been found to be stable materials that behave like vulcanized rubbers, but are thermoplastic and reprocessable. Thus, an extremely tough, rubbery plastic is obtained without the inherent disadvantages of a vulcanized rubber. These copolymerized rubber-forming monomers with the macromolecular monomers of the present invention have the additional use as an alloying agent for dispersing additional rubber for impact plastics.

Just as metal properties are improved by alloying, so are polymer properties. By adding the appropriate amount of an incompatible material to a plastic in a microdispersed phase, over-all polymer properties are improved. A small amount of incompatible polybutadiene rubber correctly dispersed in polystyrene gives high impact polystyrene. The key to this microdispersion is a small amount of chemical graft copolymer that acts as a flux for incorporating the incompatible rubber.

In a similar manner, a copolymer of the macromolecular monomer of the present invention can be flux for incorporating or dispersing incompatible polymers into new matrices making possible a whole new line of alloys, impact plastics, malleable plastics and easy-to-process plastics.

The following example illustrates the synthesis of an ethylene propylene copolymer and a series of ethylene/propylene/graft (2-polystyrene-5-norbornene) polymers by a continuous process using a continuous flow stirred tank reactor and a Ziegler catalyst system.

Example 7

Synthesis of Terpolymer of
Ethylene-Propylene-(2-Polystyrene-5-Norbornene)

| Reactor Conditions: | |
|---|---|
| Reactor | 1 Liter CFSTR |
| Temperature | 30½ C. |
| Pressure | 500 kpa |
| Agitation | 1200 kpa |
| Residence | 9 min |
| Feeds: | |
| Toluene | 4.11 kg/hr |
| Ethylene | 95 g/hr |
| Propylene | 138 g/hr |
| 2-polystyryl-5-norbornene | |
| Condition A | 0 g/hr |
| Condition B | 5.63 g/hr |
| Condition C | 11.26 g/hr |
| Condition D | 16.89 g/hr |
| Condition E | 22.52 g/hr |
| Hydrogen | 0 wppm on Ethylene |
| VCl$_4$ | 0.493 g/hr |
| Ethyl aluminum sesquichloride | |

| Polymer Characterization: | | | | | |
|---|---|---|---|---|---|
| Condition | A | B | C | D | E |
| Polymerization Rate(gms/hr) | 210 | 207 | 202 | 208 | 210 |
| Ethylene wt%[1] | 48 | 49 | 45 | 42 | 40 |
| PS wt %[2] | 0 | 8 | 11 | 15 | 19 |
| Mn by GPC | 107 k | 112 k | 111 k | 106 k | 106 k |
| Mw by GPC | 174 k | 184 k | 182 k | 172 k | 171 k |
| Tensile (psi) | 10 | 70 | 190 | 640 | 850 |
| % Elongation | 400 | 560 | 720 | 820 | 870 |

Notes:
[1]Ethylene content determined by ASTM 1246
[2]PS content is the weight percent of the incorporated 2-polystyryl-5-norbornene as determined by GPC.

Monomer conversion for this monomer is uniformly above 85% for this monomer under these polymerization conditions.

The distribution of the polystyrene grafts in the poly was determined by analyzing an aliquot of the polymer by gel permeation chromatography. The eluant of the chromatograph column was analyzed and a UV detector at 254 nm which reveals the presence of styrenic residues. In all cases the responses of these two detectors were coincident indicating that the styrenic residues are incorporated in the polymer.

The graft copolymers prepared in example 7 above are clear tough thermoplastic elastomers. Transmission electron micrographs of the grafts indicate that they are microphase separated with spherical polystyrene domains averaging 30 anometers. The rheology of the graft copolymers is typical for multiphase materials. A temperature sweep from 200° to 100° C. did not show a large change in viscosity, which indicates that the system likely remains biphasic in the melt. This corresponds to the non-newtonian shear behavior. The polymer undergoes a 4 order of magnitude drop in viscosity upon increasing the shear-rate from $10^{-2}$ to $10^{-2}$ rad/sec. The mechanical properties of the graft copolymers increase with increasing polystyrene content: the ungrafted EP has no strength. However, the sample containing 19% grafted polystyrene had a tensile of 900 psi with an elongation at break of 875%.

We claim:

1. A composition represented by the formula:

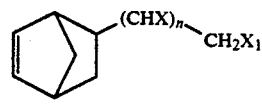

wherein n is O or an integer ranging from 1-17, X and X$_1$ are independently selected from the group consisting of H, Li, K and Na, provided that where X$_1$ is Li, K or Na, then X is H, further provided that where X$_1$ is H, then n is an integer ranging from 1-17 and (n-1) of the X substituents are also H and X is Li, K or Na, and further provided that where n is O, then X$_1$ is Li, K or Na.

2. The composition of claim 1 wherein X$_1$ is lithium.

3. A composition having the structure:

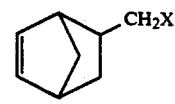

wherein X is an alkali metal selected from the group consisting of lithium, sodium and potassium.

4. The composition of claim 3 wherein X is lithium.

5. An anionic polymerization initiator comprising the composition of claim 1.

6. A process for preparing a composition represented by the formula:

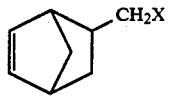

wherein X is lithium, sodium or potassium, comprising:
(a) reacting an unsaturated halide and a compound selected from cyclopentadiene and dicyclopentadiene at a temperature of at least 20° C. to form 2-halomethyl-5-norbornene; and
(b) contacting said 2-halomethyl-5-norbornene with an alkali metal selected from the group consisting of lithium, sodium or potassium, in the presence of inert nonprotonic solvents at a temperature below about 0° C.

7. The process of claim 6, wherein said unsaturated halide is allyl bromide.
8. The process of claim 6, wherein said alkali metal is lithium.
9. The process of claim 6, wherein said product of step (a) is purified by fractional distillation before step (b).
10. The process of claim 6, wherein said alkali metal is present as a suspension of the metal in a solvent and wherein said 2-halomethyl-5-norbornene is gradually added to said solvent suspension maintained at a temperature below 0° C.
11. The process of claim 10, wherein said solvent suspension is maintained at a temperature below about −30° C.
12. The process of claim 6, wherein the solvent is ether or tetrahydrofuran.

* * * * *